(12) United States Patent
Matsumoto et al.

(10) Patent No.: US 6,991,610 B2
(45) Date of Patent: Jan. 31, 2006

(54) ORTHOPEDIC FIXTURE (75) Inventors: Yoshikazu Matsumoto, Funabashi (JP);
Hiroshi Yamaguchi, Chiba (JP);
Hiroyuki Hirano, Funabashi (JP)

(73) Assignee: Alcare Co., Ltd., Tokyo (JP)

( * ) Notice: Subject to any disclaimer, the term of this patent is extended or adjusted under 35 U.S.C. 154(b) by 459 days.

(21) Appl. No.: 10/134,921

(22) Filed: Apr. 29, 2002

(65) Prior Publication Data

US 2002/0161319 A1 Oct. 31, 2002

(30) Foreign Application Priority Data

Apr. 27, 2001 (JP) ......................................... 2001-131744

(51) Int. Cl.
*A61F 5/00* (2006.01)

(52) U.S. Cl. ................... 602/4; 602/5; 602/8
(58) Field of Classification Search ................. 602/4–8; 128/878–879
See application file for complete search history.

(56) References Cited

U.S. PATENT DOCUMENTS 5,577,999 A    11/1996  Sekine et al. .................. 602/8
6,027,777 A    2/2000   Hirano et al. ............... 428/35.4
6,254,959 B1   7/2001   Hirano et al. ................. 428/71

FOREIGN PATENT DOCUMENTS

JP     7289582    11/1995
JP     9224796     9/1997

*Primary Examiner*—Michael A. Brown (74) *Attorney, Agent, or Firm*—Adams & Wilks (57) ABSTRACT

An orthopedic fixture has a support member adapted to be positioned around a diseased or injured part of a patient's body and conformed to the shape of the diseased or injured part, and at least one buffer member comprised of a mixture containing a predetermined amount of elastic granules and a predetermined amount of a water-curable resin having an elasticity after curing sufficient for bonding the elastic granules after curing of the water-curable resin. The mixture of the buffer member forms a mass before curing of the water-curable resin so that when the support member is positioned around the diseased or injured part and pressure is applied to the mass, the elastic granules move one another to shape the mass into a configuration corresponding to the shape of the diseased or injured part.

43 Claims, 4 Drawing Sheets

ORTHOPEDIC FIXTURE

BACKGROUND OF THE INVENTION

1. Field of the Invention

The present invention relates to an orthopedic fixture, such as a splint, for use in the field of orthopedic surgery and which is placed or mounted on a diseased or injured part of a patient's body so as to fix and support the diseased or injured part for the purpose of treating a bone fracture, a sprain, a dislocation or the like.

2. Background Information

In the field of orthopedic surgery, various methods are known for fixing and supporting a diseased or injured part (hereinafter referred to as the "affected part") of a patient's body by mounting or placing an orthopedic fixture over the affected part for such purposes as treating a bone fracture, a sprain, a dislocation or the like. One conventional orthopedic fixture has a glass base fabric impregnated with a water-curable resin which is characterized with a high hardness after curing. When the conventional orthopedic fixture is placed directly on the affected part, the hardness of the fixture imparts an unpleasant feeling of pain to the patient. An attempt has been made to alleviate this pain by interposing a cushion material, such as foam or an unwoven fabric, between the fixture and the affected part of the patient's body. However, while the cushion material can prevent the fixture from being in direct contact with the affected part, its fitness to the affected part, especially a thin part such as a wrist, ankle or flection, is inadequate, whereby it is sometimes impossible to securely fix the affected part.

SUMMARY OF THE INVENTION

It is an object of the present invention to provide an orthopedic fixture for fixing and supporting a diseased or injured part of a patient's body comfortably and with a sufficient holding and fixing force.

Another object of the present invention is to provide an orthopedic fixture that can be easily formed in conformity with the shape of the diseased or injured part of a patient's body.

Another object of the present invention is to provide an orthopedic fixture which can be fitted to any diseased or injured part of a patient's body, including wrist, ankle and flection.

Another object of the present invention is to provide an orthopedic fixture which has good air permeability.

Still another object of the present invention is to provide an orthopedic fixture having a simple structure and which is economical to manufacture.

The foregoing and other objects of the present invention are carried out by an orthopedic fixture comprising a flexible support member adapted to be positioned around a diseased or injured part of a patient's body and conformed to the shape of the diseased or injured part, and a buffer member disposed on the flexible support member and comprised of a mixture containing a predetermined amount of elastic granules and a predetermined amount of a water-curable resin having an elasticity after curing sufficient for bonding the elastic granules after curing of the water-curable resin.

Preferably, the buffer member has a cover for covering the mixture containing the elastic granules and the water-curable resin. The cover is comprised of a material which is inactive to the water-curable resin and which is permeable to water. The flexible support member and the buffer member are preferably covered by a covering material which is permeable to water, which is highly permeable to air, and which is inactive to the water-curable resin.

After adding water to the support member and the buffer member until the water penetrates through the cover and reaches the water-curable resin, the fixture is positioned around a diseased or injured part of a patient's body with the buffer member abutted against the diseased or injured part and conformed to the shape of the diseased or injured part. The water-curable resin is then left to cure, whereby the support member and the buffer member are rendered into one integral structure that can be detachably fixed to the diseased or injured part. In this state, the support member adequately holds the buffer member while the diseased part is softly supported by the buffer member.

BRIEF DESCRIPTION OF THE DRAWINGS

The foregoing summary, as well as the following detailed description of preferred embodiments of the invention, will be better understood when read in conjunction with the accompanying drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE PREFERRED EMBODIMENTS

While this invention is susceptible of embodiments in many different forms, this specification and the accompanying drawings disclose only some examples of the use of the invention. The invention is not intended to be limited to the embodiments so described, and the scope of the invention will be pointed out in the appended claims.

Figure 1:
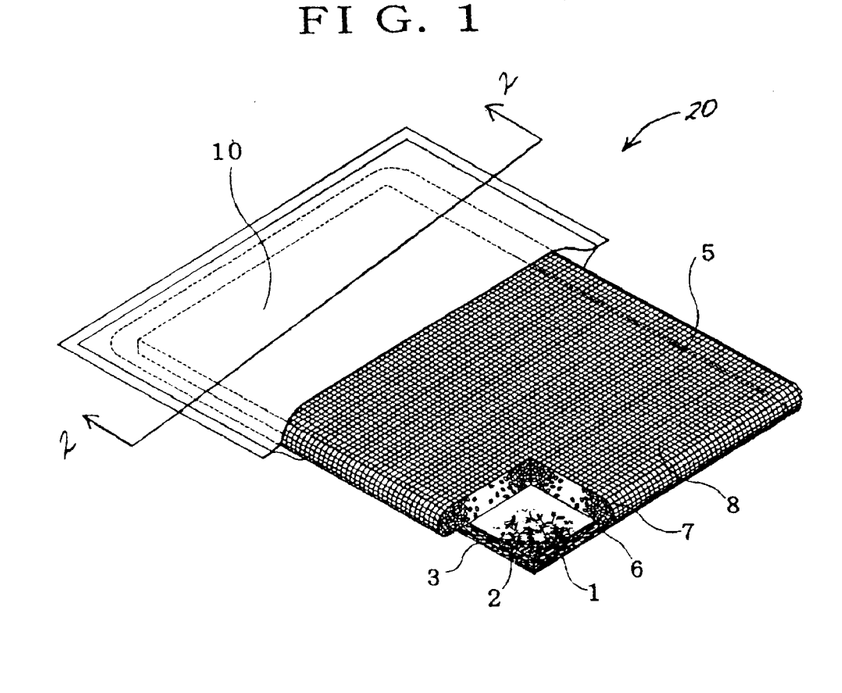
FIG. 1 is a partially cutaway perspective view showing an embodiment of an orthopedic fixture according to the present invention.
Figure 2:
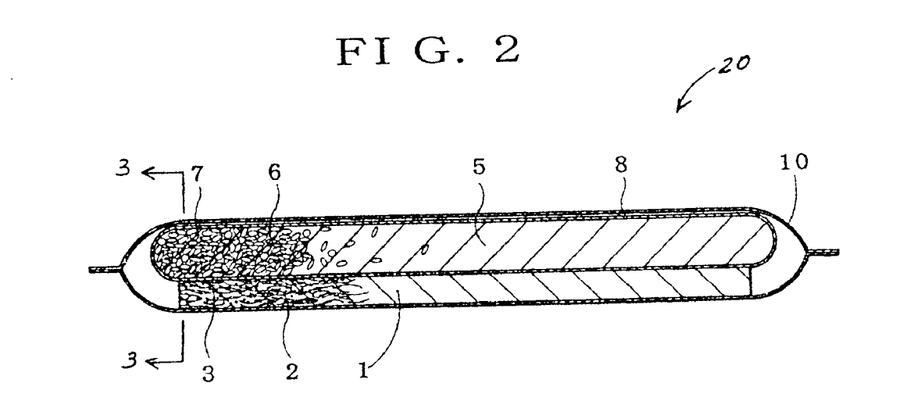
FIG. 2 is a cross-sectional taken along line 2—2 in FIG. 1.
Figure 3:
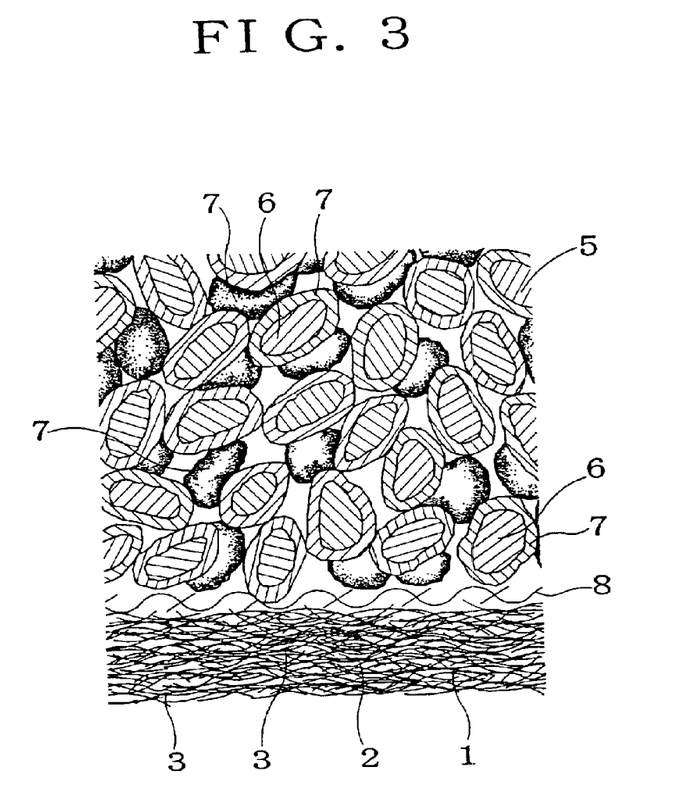
FIG. 3 is an enlarged partial cross-sectional view taken along line 3—3 in FIG. 2 with the covering material omitted.
Figure 4:
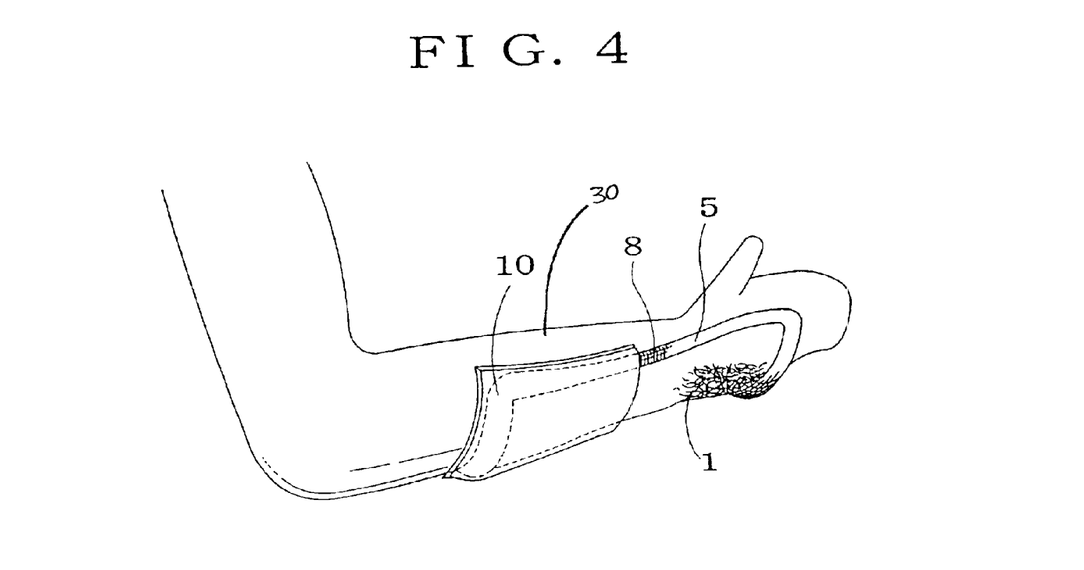
FIG. 4 is a partially cutaway perspective view showing the orthopedic fixture of the present invention in position on a diseased or injured part of a patient's body.
Figure 5:
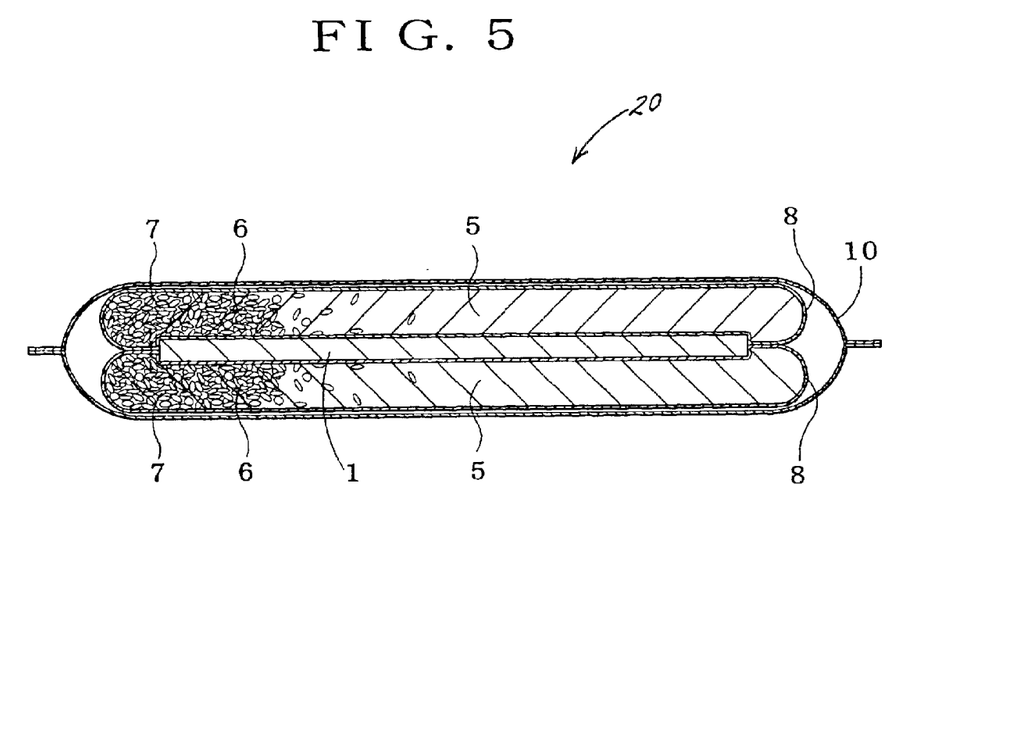
FIG. 5 is a cross-sectional view showing another embodiment of the orthopedic fixture according to the present invention.
Figure 6:
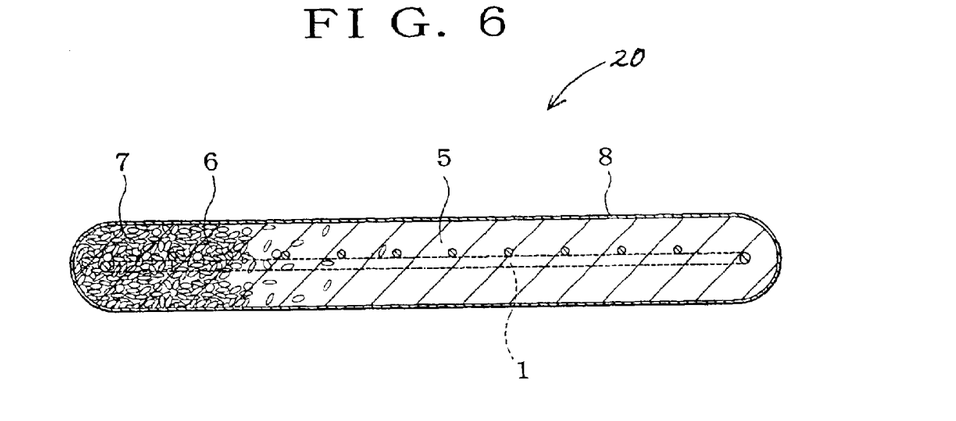
FIG. 6 is a cross-sectional view showing still another embodiment of the orthopedic fixture according to the present invention.

FIGS. 1–3 show a preferred embodiment of an orthopedic fixture, generally designated at 20, according to the present invention. FIG. 4 shows the orthopedic fixture 20 according to the present invention for supporting a diseased or injured part (hereinafter referred to as the "affected part") 30 of a patient's body. FIGS. 5 and 6 show two alternative embodiments of the orthopedic fixture 20 according to the present invention. In FIGS. 1–6, like numerals are used to indicate like elements throughout.

The orthopedic fixture 20 has a flexible support member 1 adapted to be positioned around the affected part of a patient's body and conformed to the shape of the affected part. The support member 1 comprises a base material 2 and a curable resin 3 retained (e.g., impregnated) in the base material 2. A buffer member 5 is disposed on a major surface of the support member 1 and is comprised of a mixture containing a predetermined amount of elastic granules 6 and a predetermined amount of a water-curable resin 7. The buffer member 5 has a cover 8 (i.e., first cover) for covering the mixture containing the elastic granules 6 and the water-curable resin 7. The cover 8 is comprised of a material which is inactive to the water-curable resin 7 and which is permeable to water. The support member 1 and the buffer member 5 are preferably covered by a covering material 10 (i.e., second cover) which is permeable to water, which is highly permeable to air, and which is inactive to the curable resins 3 and 7. Preferably, the buffer member 5 has a thickness of at most 3 cm while the entire thickness for the orthopedic fixture 20 is at most 5 cm.

The base material 2 of the support member 1 comprises a flexible material which can be conformed to the shape of the affected part and which is inactive to the curable resin 3. For example, natural fibers such as mixed-spun fibers, union cloth, and nonwoven fabric, and artificial fibers such as inorganic fibers, regenerated fibers, semi-synthetic fibers and synthetic fibers may be used as raw materials for the base material 2. The curable resin 3 is preferably comprised of a material having an appropriate hardness and stiffness after curing. For example, the type of curable resin 3 selected is preferably a heat-curable resin or a photo-curable resin or, more preferably, a water-curable resin.

Figure 7:
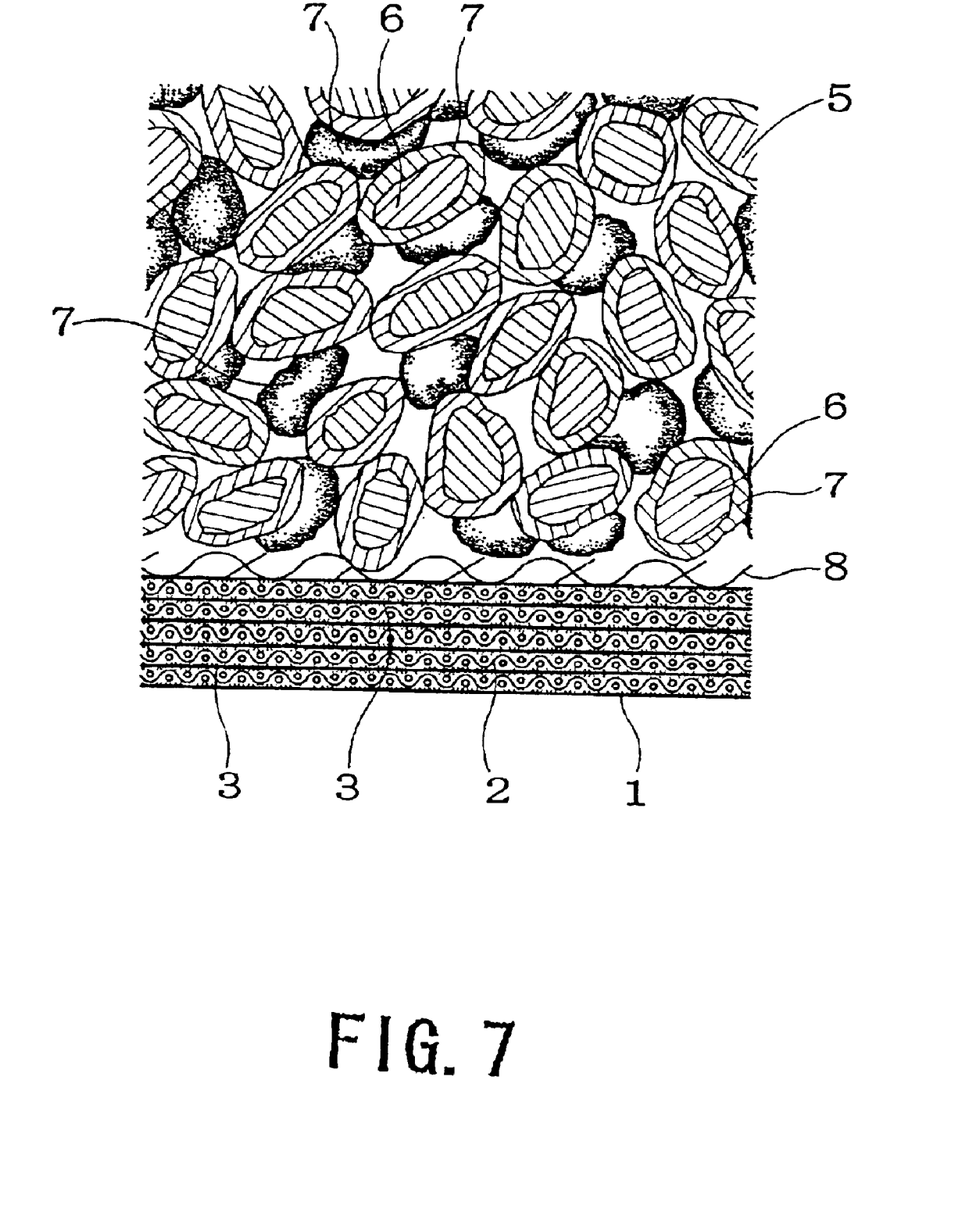
FIG. 7 is an enlarged partial cross-sectional view showing another embodiment of the orthopedic fixture according to the present invention.

In the embodiment shown in FIGS. 1–3, only one layer of the base material 2 containing the curable resin 3 is used. A single layer of the base material 2 is sufficient when the layer is thick enough to retain a sufficient amount of the curable resin 3 and to provide a strength sufficient to function as the support member 1. When a single layer of the base material 2 is insufficient, a multiple number of overlaid layers of the base material 2 is used. For example, FIG. 7 shows five overlaid layers of the base material 2 each containing the curable resin 3. When glass fibers are used for the base material 2, the support member 1 preferably has eight overlaid layers of the base material 2 containing the curable resin 3 since one layer of a glass fiber base material containing the curable resin 3 will not have sufficent strength to function as the support member 1.

The water-curable resin selected for the curable resin 3 should preferably be unstimulating and safe to human bodies and have excellent storage stability, a viscosity at ordinary temperature of from about 18 to 50 Pa·s, and a curing time at ordinary temperature of from 2 to 30 minutes. The water-curable resin selected for the curable resin 3 preferably contains a prepolymer, a catalyst, a stabilizer, a defoaming agent, and an antioxidant.

The prepolymer is preferably a mixture of a polyol and a polyisocyanate. The polyol may be polyethylene glycol, polypropylene glycol, polyester polyol, polycaprolactone diol, polyoxyethylene sorbitan ester, ethoxylated castor oil and the like. The polyisocyanate may be 4,4'-diphenylmethane diisocyanate, methylenebis-(4-cyclohexylisocyanate), 5'-naphthalene diisocyanate, xylene diisocyanate, tolylene diisocyanate, hexamethylene diisocyanate and the like.

The catalyst is preferably a tertiary amine such as 4-12-(1-methyl-2-(4-morpholinyl)ethoxy)ethyl-morpholine (MEMPE), or a morpholine type such as dimorpholinodiethylether and bis(2,6-dimethylmorpholino)diethylether, and bis(dimethylaminoethyl)ether.

Furthermore, the stabilizer is preferably an organic acid such as methanesulfonic acid and ethanesulfonic acid. The defoaming agent is preferably a siloxane copolymer such as polydimethylsiloxane are a modified product thereof. A preferred antioxidant is tetrakis[methylene-3-(3,5-di-tertiary-butyl-4-hydroxyphenyl) propionate]methane.

In the case where a heat-curable resin is used for the curable resin 3, a heat-curable resin which is softened at a temperature of 50° C. to 60° C. by hot water or hot air to form a predetermined shape and which is sufficiently cured in 5 to 10 minutes to provide sufficient fixing and holding functions is preferably used. In the case where a photo-curable resin is used for the curable resin 3, a photo-curable resin which begins to cure upon being irradiated by a predetermined quantity of light for a predetermined period of time and cures in 5 to 30 minutes to provide a sufficient holding function is preferably used.

The material for the support member 1 may also comprise a deformable material which can be bent along the outline of the shape of the affected part and which supports the affected part while maintaining its shape after deformation. Examples of such deformable materials include iron, stainless steel, titanium, a titanium alloy, aluminum, an aluminum alloy, copper, a copper alloy, various types of nickel-titanium series shape-memory alloys, and appropriate combinations thereof. These materials are processed into a support member 1 having a shape suitable for the affected part to which it is applied, including a plate-like shape, a ladder-like shape or net-like shape, and should be suitable for forming appropriate perforations in the plate-like shaped material.

As described above, the buffer member 5 is disposed on a major surface of the support member 1 and is comprised of a mixture containing a predetermined amount of the elastic granules 6 and a predetermined amount of the water-curable resin 7 having an elasticity after curing sufficient for bonding the elastic granules 6 to form a lump after curing of the water-curable resin 7. The mixture forms a mass before curing of the water-curable resin 7 which permits the elastic granules 6 to move one another to shape the mass into a configuration corresponding to the shape of the affected part.

When water is added to the buffer member 5 and the buffer member 5 is placed on and conformed to the affected part, the water-curable resin 7 gradually cures and bonds or connects respective elastic granules 6, whereby a molded product fitted to the affected part is obtained. After curing, the water-curable resin 7 has an elasticity sufficient for bonding the elastic granules 6 together to thereby support the affected part softly and securely.

The elastic granules 6 preferably have an appropriate elasticity and are inactive or processed to be inactive to an uncured water-curable resin. As the material for the elastic granules 6, olefin type granules such as polyethylene or polypropylene having an elasticity imparted by a softener or a plasticizer, or copolymers thereof, may be selected. Furthermore, granules made of vinyl acetate copolymers, polyvinyl chloride, polystyrene, polyester, polyether, polyurethane, neoprene, polybutadiene, silicone, and other rubber materials and gelled products, which have an inherent elasticity or an elasticity which is imparted, may be used.

The following commercially available granules, for example, may be used as the elastic granules 6 of the orthopedic fixture of the present invention: COSMOGEL (trade name, manufactured by COSMO INSTRUMENTS CO., LTD.); MNCS (trade name, manufactured by BRIDGESTONE CORPORATION); ALPHAGEL (trade name, manufactured by SIGEL CO., LTD.); PEF (trade name, manufactured by TORAY INDUSTRIES, INC.); MITSUFUKU FOAM (trade name, manufactured by MITSUFUKU INDUSTRY CO., LTD.); EXESEAL (trade name, manufactured by INOAC CORPORATION), KALSOFT (trade name, manufactured by TAKIRON CO., LTD.); Neoprene Rubber (manufactured by YAMAMOTO CHEMICAL IND. CO., LTD.); CR Latex (manufactured by DAIWABO CO., LTD. and MARUSHIN CHEMICAL INDUSTRIES CO., LTD.); and SILICONE SPONGE (manufactured by CHIYODA RUBBER CO., LTD., INOAC CORPORATION, and SHIN-ETSU CHEMICAL CO., LTD.).

Preferably, the granules 6 are generally spherical-, rod-, cubic-, rectangular parallelopiped-, columnar- or disk-shaped. More preferably, the granules 6 have a shape in which the corners are chipped off or rounded. Furthermore, the granules 6 may be formed into a solid or hollow body, or may be a foam. In the case that the granules 6 are comprised of a foam, it should preferably be a closed-cell foam so that the water-curable resin 7 will not permeate into the granules. For example, a closed-cell foam whose surface is covered with a thin layer of material is preferred.

The size of the granules 6 should preferably be at most about 8 $cm^3$, depending upon the part of the patient's body to which the orthopedic fixture is applied, the material used for the granules 6, and the type of water-curable resin 7 used. More preferably, the size of the granules 6 is at most 0.125 $cm^3$, by which an orthopedic fixture having a smooth surface can be obtained. Use of granules having a size larger than about 8 $cm^3$ can ensure a high air permeability, but may sometimes result in an inferior surface smoothness and adversely affect modeling of the buffer member.

It will be appreciated by those of ordinary skill in the art that a combination of two or more different types of granules comprised of the materials and having the shapes, properties and sizes as set forth above may alternatively be used for the granules 6 of the orthopedic fixture 20 according to the present invention.

The water-curable resin 7 is preferably comprised of a material having an appropriate elasticity after curing. The type of water-curable resin 7 is selected so that the granules 6 bond with the water-curable resin 7 when the water-curable resin is reacted and cured by the addition of water. Alternatively, the granules 6 may be wrapped with a material so that the granules are surrounded by the water-curable resin 7 without bonding with the water-curable resin 7.

The water-curable resin 7 is admixed to the granules 6, and this mixture is placed in a mass or a lump. A water-curable urethane prepolymer is preferably used as the water-curable resin because it can be easily and conveniently cured by the addition of water. However, other curable resins such as, for example, moisture-curable silicone resins or the like, may be used.

The water-curable urethane prepolymer of the buffer member 5 is a prepolymer having isocyanate groups at terminal ends, obtainable by the reaction of a polyol and a polyisocyanate. As the polyol, a low molecular weight polyol such as polyethylene glycol, polypropylene glycol and polyglycerol, a polyether polyol obtainable by adding alkylene oxide such as ethylene oxide or propylene oxide to a polyphenol, a polyester polyol obtainable by dehydration condensation of a low molecular weight polyol and a dicarboxylic acid such as adipic acid or phthalic acid, a polytetramethylene glycol obtainable by ring opening polymerization of a lactone such as γ-butyrolactone or ε-caprolactone, a polydiene polyol which is a polymer of a diene compound such as butadiene or isoprene and has hydroxyl groups at terminal ends, and mixtures thereof, may be used.

The average molecular weight of the polyol is preferably from about 600 to 4,000, and more preferably from about 1,000 to 2,000. It is desirable to use a polyol having one of such molecular weights or a combination thereof. It is generally preferred to use polyethylene glycol or polypropylene glycol as the polyol. In this instance, if the molecular weight is too small, the elasticity of the water-curable resin tends to be poor, and if it is too large, it tends to be highly elastic. However, a high viscosity makes it difficult to mix with the granules. The viscosity is therefore preferably from about 0.01 to 2 Pa·s, and more preferably from about 0.05 to 1 Pa·s at 20° C.

As the polyisocyanate, known organic polyisocyanates may be used. For example, the following organic polyisocyanates may be used: diphenylmethane diisocyanate; toluene diisocyanate; 1,5-naphthalene diisocyanate; tolidine diisocyanate; hexamethylene diisocyanate; isophorone diisocyanate; p-phenylene diisocyanate; transcyclohexane 1,4-diisocyanate; xylene diisocyanate; hydrogenated xylene diisocyanate; hydrogenated diphenylmethane diisocyanate; lidine diisocyanate; triphenylmethane triisocyanate; tris (isocyanatephenyl)thiophosphate; tetramethylxylene diisocyanate; lidine ester triisocyanate; 1,6,11-undecane triisocyanate; 1,8-diisocyanate-4-isocyanate methyloctane; 1,3,6-hexanemethylene triisocyanate; bicycloheptane triisocyanate; trimethylhexamethylene diisocyanate; polymethylenepolyphenylene polyisocyanate and 3-isocyanatemethyl 3,5,5-trimethylcyclohexyl isocyanate; and carbodiimide-modified or isocyanurate-modified polyisocyanates thereof.

The foregoing polyisocyanates may be used alone or as a mixture of appropriate combinations thereof. Among the above-mentioned compounds, aromatic polyisocyanates such as diphenylmethane diisocyanate, p-phenylene diisocyanate and polymethylenepolyphenylene polyisocyanate, and carbodiimide-modified polyisocyanates thereof, may be used. Furthermore, the proportions of the polyol and the polyisocyanate used is preferably from about 1.2 to 10 equivalents of polyisocyanate, preferably from about 1.5 to 5 equivalents, based on 1 equivalent of polyol.

Certain additives may be added to the water-curable resin 7, including a catalyst, a stabilizer, a defoaming agent, an antioxidant, a colorant, a thixotropy imparting agent, a filler or the like, taking into consideration the curing time, the storage stability, the acceleration of degassing during curing, the color tone on finish, or the like. As such additives, known compounds may suitably be used depending upon the components of the water-curable resin 7.

In the case in which a water-curable urethane prepolymer is used, the following catalysts, for example, may be used: bis (2,6-dimethylmorpholino)diethylether; triethylenediamine; cyclohexylamine; Dimethylethanolamine; a substituted morpholine; dimethylpiperazine; dimethylaminoethyl-3-dimethylaminopropylether; dimorpholinoethane; tetraethylethyleneamine; imidazole; triethanolamine; 1,3-bis(dimethylamino)2-propanol; dimethylaminoethoxyethanol; dimorpholinodiethylether; dimethylaminodiethylether; bis(morpholinoethyl)ether; and 4-[2-[1-methyl-2-(4-morpholinyl)ethoxy]ethyl]morpholine. These may be used alone or as a mixture thereof, and may preferably be used in an amount of from about 0.01 to 5% (% by weight) to the water-curable urethane prepolymer.

As the stabilizer, organic acids, organic acid chlorides, acidic substances such as acidic phosphates, chelating agents (diketone compounds and hydroxycarboxylic acids) and the like may be used. The type of stabilizer selected should take into consideration the type of catalyst used. Methanesulfonic acid may suitably be used as the organic acid. The amount of the stabilizer added is preferably from about 0.01 to 3%.

As the defoaming agent, silicone-type and wax-type defoaming agents may be used. Preferably, silicone-type defoaming agents are used in an amount of from about 0.01 to 2%. As the antioxidant, hindered phenols and phosphorus type compounds are suitable. A preferred antioxidant is tetrakis[methylene-3-(3-5-di-tertiary-butyl-4-hydroxyphenyl)propionate]methane. As the colorant, it is preferable to use a colorant which has a reduced risk of causing skin problems and which conforms with the Japanese Pharmaceutical Affairs Law.

Use of the thixotropy imparting agent prevents maldistribution of the water-curable resin 7 in the mixture, thereby permitting the water-curable resin 7 and the granules 6 to be maintained in the uniformly mixed state. In the case where the water-curable urethane prepolymer is used as the thixotropy imparting agent, silica, titanium oxide, polyalkylene modified compounds obtainable by treating terminal hydroxyl groups of an organic type polyalkylene glycol with a hydroxyl group-treating agent, i.e. usually, ones obtainable by treating polyethylene glycol, polypropylene glycol or a copolymer thereof with methyl chloride, fatty acid or the like, aromatic carboxylates, benzylidene sorbitol synthesized by an acetalization reaction of D-sorbitol and an aromatic aldehyde, ditrilidene sorbitols and the like, may be used. The added amounts of these additives is preferably from about 0.01 to 6%, and more preferably from about 0.05 to 3% based on the water-curable urethane prepolymer.

The physical properties of the water-curable resin 7 depend on the weight of the affected part to which the orthopedic fixture is applied. However, it is preferable to use a water-curable resin which has a curing time of from about 3 to 30 minutes after it is brought into contact with water, and which, after curing, will provide sufficient hardness to support the weight of the affected part, will be subjected to a minimal change in volume as a result of the weight being applied, will not cause pyrexia, will not stimulate the affected part of the patient's body, and will have high storage stability. For this purpose, a water-curable urethane prepolymer is preferred.

The amount of the water-curable resin 7 to be mixed with the granules 6 is preferably defined in terms of the amount of the water-curable resin per volume of the granules rather than then in terms of weight ratio. Preferably, at least about 7.5 g of the water-curable resin 7 per liter of the granules 6 is used. More preferably, an amount of from about 45 to 420 g of the water-curable resin 7 per liter of the granules 6 is used.

The mixing of the granules 6 and the water-curable resin 7 may suitably be conducted at a temperature of at least 20° C. and a relative humidity (RH) of at least 20%. The mixing is carried out with a mixing machine, such as a utility mixer, a concrete mixer or the like. For example, a mixing vessel is filled with a dried nitrogen gas, and a predetermined amount of granules 6 is poured thereinto. While stirring the granules 6 and the dried nitrogen gas, a predetermined amount of the water-curable resin 7 is added thereto, and the mixture is stirred mixed until it becomes uniform. In this state, the surfaces of the granules 6 are sufficiently covered with the uncured water-curable resin 7 to allow interconnection of the granules 6 so that the granules 6 are adhered and bonded in a mass with the water-curable resin while allowing the granules 6 to move one another when pressure is applied to the orthopedic fixture.

After the granules 6 and the uncured water-curable resin 7 are uniformly mixed, the resulting mixture, which forms a mass as described above, may be stored without being cured by disposing it directly into a packaging bag which is preferably comprised of aluminum foils or the like. Alternatively, the mass is stored in a box or container which is not permeable to moisture.

The cover 8 is preferably comprised of water-permeable material which is inactive to the water-curable resin 7 and which has openings which are smaller in size than the elastic granules 6 so as to prevent the elastic granules 6 from flowing out while allowing water to permeate therethrough. For example, the material for the cover 8 should not have a chemical structure nor contain a substance which activates the reactive groups of the water-curable resin. The particular size, shape and structure of the cover 8 can be selected depending on the affected part to which it is to be applied.

As the material for the cover 8, a knit, a woven fabric or unwoven fabric formed by yarns made of bundles of fibers, or a mesh-like material made of monofilaments, may be used. Preferably, a material having excellent deformability or a material which can be elongated by at least about 15% in at least one direction is selected for the cover 8. For example, synthetic fibers of polyester, polypropylene, polyethylene, polyacryl, polyurethane, a styrene-isoprene-styrene copolymer (SIS) and polyamide, regenerated fibers and natural fibers such as staple fibers, rayon, cotton and linen, and inorganic fibers such as glass fibers, may be used. If a material which is reactive to the water-curable resin 7 or which has a high moisture is selected, it is preferred to make the material inactive with the water-curable resin by preliminarily treating the surface of the material, and to remove the moisture by drying.

When a water-curing urethane prepolymer is selected as the material for the water-curable resin 7, polyester, polypropylene, polyethylene, polyurethane, SIS and the like, which are not reactive to the uncured urethane prepolymer, are preferably used for the material of the cover 8. More preferably, polyester, polypropylene, polyethylene, polyurethane, SIS and the like which have a heat sealing property, and single-spun fibers or mixed-spun fibers thereof, are used for the material of the cover 8.

The finished state of the cover 8 is preferably a knit, woven fabric, an unwoven fabric or a net-like structure. More preferably, the finished state of the cover 8 is a knit or unwoven fabric structure which has sufficient flexibility and elasticity to allow the cover 8 and the mixture contained therein to be shaped in conformity with the contour of the affected part to which the orthopedic fixture is applied. Preferably, the material and structure selected for the cover 8 should be able to undergo elongation of at least 15% in any one of the longitudinal and transverse directions. If the degree of elongation is less than 15%, it may sometimes be difficult to shape the cover 8 mixture contained therein in conformity with the contour of the affected part.

The knit, woven fabric and the like used for the cover 8 may be formed by bundling a lot of thin fibers. In such a case, it is preferred to conduct a treatment to lower the affinity of the cover 8 to the water-curable resin 7 in order to prevent the water-curable resin from penetrating into the thin fibers. For example, the knit, woven fabric and the like may be treated with, for example, a fluorine-type, a silicone-type, a paraffin-type, an alkylchlomic chloride-type, an alkylmethylpyridium chloride-type and an alkylethylene urea-type treating agent. In one example, the treating agent is used in such an amount that the active ingredient would be attached onto the surface of the cover 8 in an amount of from about 0.1 to 6%. In another example, when a treating agent of a fluorine-type emulsion is used in an amount such that the active ingredient would be attached onto the surface of the cover 8 in an amount of about 0.7%, the stability of the cover 8 during storage is further improved. The treating agent may be attached by impregnating, coating, spraying or the like, before or after the preparation of the knit, woven fabric and the like.

In a preferred embodiment, the cover 8 is prepared by knitting yarns made of polypropylene or polyester alone or a blend thereof in a cylindrical shape with a weight (METSUKE) of about 100 to 300 g/m$^2$ and more preferably about 230 g/m$^2$, and a stretchability of from 5 to 60% in a longitudinal direction and from 50 to 300% in a transverse direction. For example, "WHITE NET" (trade name, manufactured by ALCARE CO., LTD.) is suitable for the cover 8.

When the buffer member 5 is exposed to water, such as by spraying or dipping in water, and the water-curable resin is cured, the buffer member 5 should preferably have the following physical properties:

(a) Hardness: from 10 to 90, and preferably from 15 to 60, in terms of Askar F hardness (measured with an F-model analogue hardness tester, manufactured by Kobunshi Keiki K.K.).

(b) Compressive strength: at most 19.6 N/cm$^2$, preferably at most 9.8 N/cm$^2$, in terms of 25% compressive strength (in accordance with JIS K6401 5.4).

(c) Compressive residual strain: at most 10% (in accordance with JIS K6401 5.5).

(d) Flexural strength: at least 39.6 N (in accordance with JIS A4-8) (test conditions: test piece has a size of 75 mm×75 mm and a thickness of 20 mm, a distance between the supports is 50 mm, and the test speed is 20 mm/min.).

As best shown in FIG. 2, the support member 1 and the buffer member 5 are preferably covered with the covering material 10 which is permeable to air and water, which has a low water absorption property and a good flexibility (low modulus and extendable), and which is inactive to the curable resins 3 and 7 of the support member 1 and the buffer member 5, respectively. It is desirable that the covering material 10 have a size such that it can cover at least the entire surface of an outer side of the support member 1 and a part of the periphery of the inner side surface of the support member 1 (surface at the side on which the buffer member 1 is provided).

Any of the materials described above for the cover 8 may be used for the covering material 10. However, it is preferred to treat the surface of the covering material 10 with a water repellant substance so that it has high water drainage after it is exposed to water. If polyester is selected for the covering material 10, no such treatment is required due to the high drainage property of polyester. For example, a polyester unwoven cloth having a weight (METSUKE) of 68 g/m$^2$, and a maximum elongation of 45% in a longitudinal direction and 120% in a transverse direction, may be used. This polyester unwoven cloth may be obtained by, for example, a dry method (such as a resin adhesion-type, a needle punch-type, a stitch bond-type, a thermal bond-type and a spun lace-type), a wet method, a melt flow-type method, and a melting type-method (spun bond-type).

In an alternative embodiment, the covering material is not used in connection with the orthopedic fixture 2. In this case, after the buffer member 5 is placed on one main surface of the support member 1, it is preferred to provide a surface-protecting material which covers the exposed opposite main surface of the support member 1. The surface-protecting material can be integrated with the buffer member 5 so that application of the support member 1 is facilitated. Furthermore, when a curable resin is used for the support member 1, it is preferred to use a surface-protecting material which is inactive to the resin component and which is capable of being peeled from the resin component. For example, films of polyethylene or polypropylene and the like treated with silicone or TEFLON material and having a thickness of preferably 10 to 5,000 µm, and more preferably 30 to 50 µm, may be used. The WHITE NET material described above for the cover 8 may also be used for the surface-protecting material, but materials which have been treated with a water-repellent substance are preferred. The openings of the WHITE NET material should be preferably sealed so that they are not penetrated by the support member 1.

An explanation of the use of the orthopedic fixture 20 of the present invention is described below for the embodiment shown in FIGS. 1 and 2 and for which a water-curable resin is selected for each of the curable resins 3 and 7 of the support member 1 and the buffer member 5, respectively.

The orthopedic fixture 20, including the covering material 10, is dipped in water so that the water penetrates through the covering material 10 and reaches the water-curable resins 3 and 7. The orthopedic fixture 20 is then removed from the water and is lightly squeezed to remove excess water. Alternatively, the excess water may be removed by drying the surface of the covering material 10 at the buffer member 5 side with dry towels. Thereafter, as shown in FIG. 4, the orthopedic fixture 20 is applied on the affected part 30 of the patient's body so that the surface of the covering material 10 on the buffer member 5 side is directly contacted with the affected part 30. Pressure is then applied to the orthopedic fixture 20, such as by pressing the support member 1 against the surface of the buffer member 5, causing the granules 6 of the buffer member 5 to move one another to shape the orthopedic fixture into a mold having a configuration corresponding to the contour of the affected part 30. In this state, the water-curable resins 3 and 7 of the support member 1 and the buffer member 5, respectively, are allowed to cure so that the support member 1, the buffer member 5 and the covering material 10 are rendered into one integral structure which is specifically shaped to conform to the affected part 30. After curing of the water-curable resin, the buffer member 5 has a soft structure which provides a cushion-like support for the affected part 30 while the support member 1 has a stiff structure which provides a firmer support for the affected part 30 as compared to the buffer member 5. The orthopedic fixture 20 applied on the affected part 30 is then fixed to the affected part by wrapping, for example, an elastic bandage (not shown) around the orthopedic fixture and the affected part. The orthopedic fixture 20 can be removed from the affected part 30 by loosening the elastic bandage.

In the embodiment shown in FIGS. 1–2, the buffer member 5 is disposed on a major surface of the support member 1 and both are covered with the covering material 10 to form an integrated body. FIG. 5 shows another embodiment of the orthopedic fixture 20 in which two buffer members 5 are provided, the support member 1 is disposed or sandwiched therebetween, and these are covered with a covering material 10 to form an integrated body. In the embodiments of FIGS. 1–2 and 5, the buffer members 5 are slightly larger than the support member 1 to facilitate handling of the orthopedic fixture 20.

FIG. 6 shows another embodiment of the orthopedic fixture according to the present invention in which the support member 1 is embedded in the buffer member 5 enveloped by the cover 8. For example, the support member 1 may be comprised of a metallic net embedded in the granules 6 of the buffer member 5. The buffer member 5 and the embedded support member 1 are enveloped by the cover 8 to form an integrated body without a covering material 10.

The method of use of the orthopedic fixture 20 according to the embodiments described above with reference to FIGS. 5 and 6 is the same as described above for the embodiment of FIGS. 1–2. Furthermore, the materials and construction for the support members 1, the buffer members 5 and the covering materials 10 of the orthopedic fixture 20 in the embodiments of FIGS. 5–6 may be the same as those described above for the embodiment of the orthopedic fixture 20 shown in FIGS. 1–2. Likewise, the covering material 10 may be omitted from the orthopedic fixtures 20 of the embodiments of FIGS. 5–6 and substituted with a surface-protecting material as described above for the embodiment of FIGS. 1–2.

The following example has been conducted to show the advantageous features of the orthopedic fixture according to the present invention.

Preparation of Support Member

Into a reaction container wherein the internal air has been purged with nitrogen gas, 384 g of polypropylene ether diol and 2 g of polydimethyl siloxane were charged. The moisture content was removed at 80 to 120° C., a portion of 1.3 g of methanesulfonic acid was added thereto, and then 467.2 g of 4,4-diphenylmethane diisocyanate was added, followed by reaction at 50 to 90° C. Further, 20 g of bis(dimethylaminoethyl)ether, the remaining portion of the methanesulfonic acid, and 20 g of propionate]methane were added, and stirring was conducted for about 1 hour to obtain a polyurethane resin composition. The polyurethane resin composition was sealed in an airtight container wherein the internal air was purged with nitrogen gas.

The polyurethane resin composition was then coated on a base fabric. As the base fabric, a tape-like base material obtained by using glass fibers ECG 75 1/0 1.0 Z and a raschel fabric in a width of 10 cm with a density of 14 lines/inch in a warf direction and 15 lines/inch in a weft direction and with a weight (METSUKE) of about 310 g/m², followed by heat cleaning, was used. The coating operation of the polyurethane resin composition on the base fabric was conducted by coating about 210 g/m² of the polyurethane resin composition using a roller coating method in a workroom maintained at a low temperature condition.

The polyurethane resin composition had a viscosity of 23.5 Pa·s and was hardly separated from the base fabric, whereby a stable support member was obtained. After being exposed to water, the support member was sufficiently applied to the affected part within a working period of 2 minutes 15 seconds. This period of time is sufficient to apply the support member even to complicated affected parts by conventional casting techniques.

After the working period elapsed, the strength of the support member increased rapidly and its plasticity lowered so that the support member retained the molded shape conforming to the shape of the affected part. For example, after exposure to water, the strength of the support member became 88 N after 5 minutes, 245 N after 10 minutes, 862 N after 40 minutes, and 1,666 N after 24 hours.

The strength of the obtained support member 1 was measured as follows. The base material coated with the polyurethane resin composition was cut into lengths of 100 mm to form test piece elements. Eight of the test piece elements were overlaid on one another. The test piece elements were immersed in water and then the water was drained so that water did not drip from the test piece elements, and a load of 1 kg was applied for 1 minute, thereby preparing the test piece elements of the support member. A three-point bending test of the test pieces was conducted with a compression tester to measure the maximum load. (Size of each test piece: length 100 mm×width 100 mm; distance between the supports: 50 mm; test speed: 25 mm/min.; and temperature of measurement: 20° C.).

Preparation of Buffer Member

A water-curable urethane prepolymer was prepared by mixing the following blend materials: 657 g of PPG 2000 (polypropylene glycol having a number average molecular weight of 2,000), 195 g of MDI (4,4'-diphenylmethane diisocyanate), 6 g of UCAT 660M (a mixture of bis(2-dimethylaminoethyl)ether and dipropylene glycol (manufactured by WITCO CO., LTD.), 1 g of IRGANOX 1010 (a hindered phenol type antioxidant), 1 g of byk-A525 (a silicone type defoaming agent), and 5 g of benzoyl chloride.

The tensile strength (at the time of 25% elongation) of the water-curable urethane prepolymer after curing was 19.6 N/cm². The tensile strength was measured with a tensile strength tester (size of test piece: length 150 mm, width 25 mm and thickness 100 μm; free length of test piece between grips: 100 mm; test speed: 100 mm/min; measurement temperature: 20° C.).

As the granules, granules of "COSMOGEL 04" of polystyrene with a spherical shape having a volume of 0.03 cm³ per granule (manufactured by COSMO INSTRUMENTS CO., LTD.) were prepared. To the granules, 170 g of the water-curable urethane prepolymer was added per liter of the granules, and these were thoroughly mixed so that the resin covered the entire surface of the granules. The resulting mixture had an adequate elasticity.

The granules coated with the water-curable urethane prepolymer were formed into a mass or lump and then entirely covered with a cover made of a water-permeable material. As the water-permeable material, a tubular bandage of a knitted fabric of polypropylene was used. For forearms, WHITE NET material (manufactured by ALCARE CO., LTD.) cut into a width of 10 cm and a length of 35 cm was used for the tubular bandage. 30 to 40 g of the granules coated with the water-curable urethane prepolymer were placed into the tubular bandage through an opening thereof and then the opening was sealed. For lower thighs, WHITE NET material cut into a width of 12.5 cm and a length of 55 cm was used for the tubular bandage. 50 to 60 g of granules coated with the water-curable urethane prepolymer were placed into the tubular bandage through an opening thereof and then the opening was sealed.

The exothermic temperature of the buffer member was 38.1° C. so that patients would not be influenced by heat generated by the buffer member (e.g., the buffer member will not burn the patients). The exothermic temperature was measured by immersing the buffer member in water at 20° C. and then taken out from the water. The water was then drained and the buffer member was placed on a flat bench. Into the center portion of the buffer member, a digital thermometer was inserted to measure the maximum temperature.

Preparation of the Orthopedic Fixture

The support member having a slightly shorter length than the buffer member was placed on the buffer member as prepared above to form an integral structure. When used to support forearms, five overlaid layers of the support member each having a length of 30 cm and a width of 7.5 cm were used. When used to support lower thighs, seven overlaid layers of the support member each having a length of 50 cm and a width of 10 cm were used. The integrated structure was covered with a covering material made of polypropylene fibers.

Use of the Orthopedic Fixture

The orthopedic fixture, including the covering material, was dipped in water until the water penetrated through the covering material and reached the water-curable resin of the support member and the buffer member. The orthopedic fixture was then removed from the water and was lightly squeezed to remove excess water. Thereafter, the orthopedic fixture was applied on the affected part of the patient's body so that the surface of the covering material on the buffer member side was directly contacted with the affected part. Pressure was then applied to the orthopedic fixture, such as by pressing the fixing member against the surface of the buffer member, causing the granules of the buffer member to move one another to shape the orthopedic fixture into a mold having a configuration conforming to the contour of the affected part. In this state, the water-curable resin of the support member and the buffer member were allowed to cure so that the support member, the buffer member and the covering material were rendered into one integral structure which was specifically shaped to conform to the affected part. After curing of the water-curable resin, the buffer member had a soft structure which provided a cushion-like support for the affected part while the support member had a stiff structure which provided a firmer support for the affected part. The orthopedic fixture applied on the affected part was then fixed to the affected part by wrapping, for example, an elastic bandage (not shown) around the orthopedic fixture and the affected part. Removal of the orthopedic fixture was accomplished by loosening the elastic bandage.

According to the present invention, during use of the orthopedic fixture the surface of the covering material at the buffer member side is made to abut the affected part of the patient's body. As a result, the granules of the buffer member can easily move one another to effectively shape the orthopedic fixture into a mold having a configuration conforming to the contour of the affected part. Particularly, it is possible to achieve a proper fit of the orthopedic fixture to thin portions of the patient's body, such as a wrist or an ankle, which has been difficult to do with conventional orthopedic fixtures. Furthermore, since the buffer member has a soft structure after curing of the curable resin and is supported by the support member which is stiffer than the buffer member, the affected part to which the orhtopedic fixture is applied can be surrounded three-dimensionally and be softly and securely held.

Thus the present invention provides an orthopedic fixture for fixing and supporting a diseased or injured part of a patient's body comfortably and with a sufficient holding and fixing force. The orthopedic fixture can be easily formed in conformity with the shape of the diseased or injured part of the patient's body and can be fitted to any diseased or injured part, including wrists, ankles and flections. The orthopedic fixture has good air permeability and has a simple structure which is economical to manufacture.

From the foregoing description, it can be seen that the present invention comprises an improved orthopedic fixture.

It will be appreciated by those skilled the art that obvious changes could be made to the embodiments described in the foregoing description without departing from the broad inventive concept thereof. It is understood, therefore, that this invention is not limited to the particular embodiments disclosed, but is intended to cover all modifications thereof which are within the scope and spirit of the invention as defined by the appended claims.

We claim:

1. An orthopedic fixture comprising: a support member adapted to be positioned around a diseased or injured part of a patient's body and conformed to the shape of the diseased or injured part; a buffer member disposed on the flexible support member and comprised of a mixture containing a predetermined amount of elastic granules and a predetermined amount of a water-curable resin having an elasticity after curing sufficient for bonding the elastic granules after curing of the water-curable resin; and a water-permeable material covering the support member and the mixture containing the elastic granules and the water-curable resin.

2. An orthopedic fixture according to claim 1; further comprising a cover for covering the mixture containing the elastic granules and the water-curable resin.

3. An orthopedic fixture according to claim 2; wherein the cover is comprised of a material which is permeable to water.

4. An orthopedic fixture according to claim 3; wherein the water-permeable material of the cover is inactive to the water-curable resin.

5. An orthopedic fixture according to claim 2; wherein the cover for covering the mixture containing the elastic granules and the water-curable resin is separate and independent from the support member.

6. An orthopedic fixture according to claim 1; wherein the support member comprises a flexible base material and a curable resin having a preselected stiffness after curing.

7. An orthopedic fixture according to claim 6; wherein the curable resin comprises a water-curable resin.

8. An orthopedic fixture according to claim 1; wherein the support member is made of a metallic material.

9. An orthopedic fixture according to claim 1; wherein the support member is disposed on one of two opposed major surfaces of the buffer member.

10. An orthopedic fixture according to claim 1; wherein the water-permeable material is inactive to the water-curable resin.

11. An orthopedic fixture according to claim 1; wherein the buffer member has a length greater than that of the support member, a first major surface disposed in contact with a major surface of the support member, and a second major surface opposite the first major surface for abutting the diseased or injured part of the patient's body.

12. An orthopedic fixture according to claim 1; wherein the buffer member is disposed on the support member so that the buffer member is interposed between the support member and the diseased or injured part of the patient's body when the support member is positioned around the diseased or injured part.

13. An orthopedic fixture comprising: a pair of buffer members each comprised of a mixture containing a predetermined amount of elastic granules and a predetermined amount of a water-curable resin having an elasticity after curing sufficient for bonding the elastic granules after curing of the water-curable resin; and a support member disposed between the buffer members and adapted to be positioned around a diseased or injured part of a patient's body and conformed to the shape of the diseased or injured part.

14. An orthopedic fixture according to claim 13; further comprising a pair of covers for covering the mixture containing the elastic granules and the water-curable resin of the respective buffer members.

15. An orthopedic fixture according to claim 14; wherein each of the covers is comprised of a material which is permeable to water.

16. An orthopedic fixture according to claim 15; wherein the water-permeable material of each of the covers is inactive to the water-curable resin.

17. An orthopedic fixture according to claim 14; further comprising a covering material covering the support member and the buffer members, the covering material being permeable to water and inactive to the water-curable resin.

18. An orthopedic fixture according to claim 13; wherein the support member comprises a flexible base material and a curable resin having a preselected stiffness after curing.

19. An orthopedic fixture according to claim 18; wherein the curable resin comprises a water-curable resin.

20. An orthopedic fixture according to claim 13; wherein the support member is made of a metallic material.

21. An orthopedic fixture according to claim 13; further comprising a covering material covering the support member and the buffer members.

22. An orthopedic fixture according to claim 21; wherein the covering material is permeable to water and is inactive to the water-curable resin.

23. An orthopedic fixture according to claim 13; wherein the pair of buffer members are disposed on the support member so that one of the buffer members is interposed between the support member and the diseased or injured part of the patient's body when the support member is positioned around the diseased or injured part.

24. An orthopedic fixture comprising: a support member adapted to be positioned around a diseased or injured part of a patient's body and conformed to the shape of the diseased or injured part; at least one buffer member comprised of a mixture containing a predetermined amount of elastic granules and a predetermined amount of a water-curable resin having an elasticity after curing sufficient for bonding the elastic granules after curing of the water-curable resin, the mixture forming a mass before curing of the water-curable resin so that when the support member is positioned around the diseased or injured part and pressure is applied to the mass, the elastic granules move one another to shape the mass into a configuration corresponding to the shape of the diseased or injured part; a first cover for covering the mixture containing the elastic granules and the water-curable resin; and a second cover for covering the first cover and the support member.

25. An orthopedic fixture according to claim 24; wherein the first cover is comprised of a material which is permeable to water.

26. An orthopedic fixture according to claim 25; wherein the water-permeable material of the first cover is inactive to the water-curable resin.

27. An orthopedic fixture according to claim 24; wherein the support member comprises a flexible base material and a curable resin having a preselected stiffness after curing.

28. An orthopedic fixture according to claim 27; wherein the curable resin comprises a water-curable resin.

29. An orthopedic fixture according to claim 24; wherein the support member is made of a metallic material.

30. An orthopedic fixture according to claim 24; wherein the support member is disposed on one of two opposed major surfaces of the buffer member.

31. An orthopedic fixture according to claim 24; wherein the second cover is made of a water-permeable material.

32. An orthopedic fixture according to claim 31; wherein the water-permeable material is inactive to the water-curable resin.

33. An orthopedic fixture according to claim 24; wherein the buffer member has a length greater than that of the support member, a first major surface disposed in contact with a major surface of the support member, and a second major surface opposite the first major surface for abutting the diseased or injured part of the patient's body.

34. An orthopedic fixture according to claim 24; wherein the second cover is made of a covering material which is permeable to water and is inactive to the water-curable resin.

35. An orthopedic fixture according to claim 24; wherein the at least one buffer member comprises a pair of buffer members; and wherein the support member is disposed between the buffer members.

36. An orthopedic fixture according to claim 24; wherein the each of the first and second covers is made of a water-permeable material.

37. An orthopedic fixture according to claim 36; wherein the water-permeable material of each of the first and second covers is inactive to the water-curable resin.

38. An orthopedic fixture according to claim 24; wherein the first cover is separate and independent from the support member.

39. An orthopedic fixture comprising:
a buffer member comprised of a mixture containing a predetermined amount of elastic granules and a predetermined amount of a water-curable resin having an elasticity after curing sufficient for bonding the elastic granules after curing of the water-curable resin;
a support member embedded in the mixture containing the elastic granules and the water-curable resin and adapted to be positioned around a diseased or injured part of a patient's body and conformed to the shape of the diseased or injured part; and
a cover for covering the support member and the mixture containing the elastic granules and the water-curable resin.

40. An orthopedic fixture according to claim 39; wherein the cover is comprised of a material which is permeable to water and inactive to the water-curable resin.

41. An orthopedic fixture according to claim 39; wherein the support member comprises a metallic net.

42. An orthopedic fixture according to claim 39; wherein the buffer member has a length greater than that of the support member.

43. An orthopedic fixture comprising: a support member adapted to be positioned around a diseased or injured part of a patient's body and conformed to the shape of the diseased or injured part; a buffer member disposed on the flexible support member and comprised of a mixture containing a predetermined amount of elastic granules and a predetermined amount of a water-curable resin having an elasticity after curing sufficient for bonding the elastic granules after curing of the water-curable resin; and a water-permeable material covering the mixture containing the elastic granules and the water-curable resin.

* * * * *